(12) United States Patent
Boire

(10) Patent No.: US 11,305,039 B2
(45) Date of Patent: Apr. 19, 2022

(54) POLYMERIC VASCULAR GRAFTS WHICH INDUCE NEOVASCULARIZATION WITH MILD TO MINIMAL INFLAMMATION AND PROMOTION OF FIBROVASCULAR TISSUE

(71) Applicant: Vanderbilt University, Nashville, TN (US)

(72) Inventor: Timothy C. Boire, Nashville, TN (US)

(73) Assignees: Vanderbilt University, Nashville, TN (US); Venostent, Inc., Nashville, TN (US)

( * ) Notice: Subject to any disclaimer, the term of this patent is extended or adjusted under 35 U.S.C. 154(b) by 86 days.

(21) Appl. No.: 16/824,674

(22) Filed: Mar. 19, 2020

(65) Prior Publication Data
US 2020/0297899 A1    Sep. 24, 2020

Related U.S. Application Data

(60) Provisional application No. 62/820,785, filed on Mar. 19, 2019.

(51) Int. Cl.
*A61L 31/06*    (2006.01)
*A61K 9/00*    (2006.01)
*A61L 31/14*    (2006.01)
*A61K 47/34*    (2017.01)

(52) U.S. Cl.
CPC ............ *A61L 31/06* (2013.01); *A61K 9/0024* (2013.01); *A61K 47/34* (2013.01); *A61L 31/146* (2013.01); *A61L 31/148* (2013.01); *A61L 2400/16* (2013.01)

(58) Field of Classification Search
CPC ...... A61L 31/06; A61L 31/146; A61L 31/148; A61L 2400/16; A61K 9/0024; A61K 47/34
See application file for complete search history.

(56) References Cited

PUBLICATIONS

Woodward et al, Porous PCL-PLLA semi-IPNs as superior, defect-specific scaffolds with potential for cranial bone defect repair, Biomacromolecules; 18(12): 4075-4083 (Year: 2017).*
Boire et al, Pendant Allyl Crosslinking as a Tunable Shape Memory Actuator for Vascular Applications, Acta Biomater; 24: 53-63. (Year: 2015).*
Boire TC, Balikov DA, Lee Y, Guth CM, Cheung-Flynn J, Sung H-J. Biomaterial-Based Approaches to Address Vein Graft and Hemodialysis Access Failures. Macromolecular Rapid Communications 2016;37(23):1860-1880.
George SJ, Izzat MB, Gadsdon P, Johnson JL, Yim APC, Wan S, Newby AC, Angelini GD, Jeremy JY. Macro-porosity is necessary for the reduction of neointimal and medial thickening by external stenting of porcine saphenous vein bypass grafts. Atherosclerosis 2001;155(2):329-336.

(Continued)

*Primary Examiner* — Carlos A Azpuru
(74) *Attorney, Agent, or Firm* — Stites & Harbison PLLC; Richard S. Myers, Jr.

(57) ABSTRACT

The present invention relates generally to shape memory polymer devices that are porous. The porosity of the device may generate advantageous neovascularization, decrease inflammation, and decrease fibrosis. The device may include a surface having a pore size of 500-750 microns and a pore spacing of 220-250 microns.

20 Claims, 15 Drawing Sheets

(56) References Cited

PUBLICATIONS

Mehta D, George SJ, Jeremy JY, Izzat MB, Southgate KM, Bryan AJ, Newby AC, Angelini GD. External stenting reduces long-term medial and neointimal thickening and platelet derived growth factor expression in a pig model of arteriovenous bypass grafting. Nat Med 1998;4(2):235-239.

Jeremy JY, Gadsdon P, Shukla N, Vijayan V, Wyatt M, Newby AC, Angelini GD. On the biology of saphenous vein grafts fitted with external synthetic sheaths and stents. Biomaterials 2007;28(6):895-908.

Longchamp A, Alonso F, Dubuis C, Allagnat F, Berard X, Meda P, Saucy F, Corpataux J-M, Déglise S, Haefliger J-A. The use of external mesh reinforcement to reduce intimal hyperplasia and preserve the structure of human saphenous veins. Biomaterials 2014.

Maurus PB, Kaeding CC. Bioabsorbable implant material review. Operative Techniques in Sports Medicine 2004;12(3):158-160.

Vijayan V, Shukla N, Johnson JL, Gadsdon P, Angelini GD, Smith FCT, Baird R, Jeremy JY. Long-term reduction of medial and intimal thickening in porcine saphenous vein grafts with a polyglactin biodegradable external sheath. J Vasc Surg 2004;40.

Boire TC, Gupta MK, Zachman AL, Lee SH, Balikov DA, Kim K, Bellan LM, Sung H-J. Pendant allyl crosslinking as a tunable shape memory actuator for vascular applications. Acta Biomaterialia 2015;24:53-63.

Lake SP, Ray S, Zihni AM, Thompson Jr DM, Gluckstein J, Deeken CR. Pore size and pore shape—but not mesh density—alter the mechanical strength of tissue ingrowth and host tissue response to synthetic mesh materials in a porcine model of ventral hernia repair. Journal of the Mechanical Behavior of Biomedical Materials 2015;42:186-197.

Zhang Z, Wang Z, Liu S, Kodama M. Pore size, tissue ingrowth, and endothelialization of small-diameter microporous polyurethane vascular prostheses. Biomaterials 2004;25(1):177-187.

Zhu L-M, Schuster P, Klinge U. Mesh implants: An overview of crucial mesh parameters. World Journal of Gastrointestinal Surgery 2015;7(10):226-236.

Klosterhalfen B, Klinge U. Retrieval study at 623 human mesh explants made of polypropylene—impact of mesh class and indication for mesh removal on tissue reaction. Journal of Biomedical Materials Research Part B: Applied Biomaterials 2013:n/a-n/a.

Greca FH, Souza-Filho ZA, Giovanini A, Rubin MR, Kuenzer RF, Reese FB, Araujo LM. The influence of porosity on the integration histology of two polypropylene meshes for the treatment of abdominal wall defects in dogs. Hernia 2008;12(1):45-49.

Klinge U, Klosterhalfen B. Modified classification of surgical meshes for hernia repair based on the analyses of 1,000 explanted meshes Hernia 2012;16(3):251-258.

Karageorgiou V, Kaplan D. Porosity of 3D biomaterial scaffolds and osteogenesis. Biomaterials 2005;26(27):5474-5491.

Roosa SMM, Kemppainen JM, Moffitt EN, Krebsbach PH, Hollister SJ. The pore size of polycaprolactone scaffolds has limited influence on bone regeneration in an in vivo model. Journal of Biomedical Materials Research Part A 2010;92A(1):359-368.

Yang Y, Liu F, Tang M, Yuan M, Hu A, Zhan Z, Li Z, Li J, Ding X, Lu L. Macrophage polarization in experimental and clinical choroidal neovascularization Scientific Reports 2016;6:30933.

Marchant DJ, Bellac CL, Moraes TJ, Wadsworth SJ, Dufour A, Butler GS, Bilawchuk LM, Hendry RG, Robertson AG, Cheung CT and others. A new transcriptional role for matrix metalloproteinase-12 in antiviral immunity. Nature Medicine 2014;20:493.

Wong MD, Bingham K, Moss E, Warn JD, Smirnov I, Bland KS, Starcher B, Franano FN, Burke SK. Recombinant Human Elastase Treatment of Cephalic Veins. Cardiovascular pharmacology: open access 2016;5(2):178.

Boire, et al., Effect of pore size and spacing on neovascularization of a biodegradble shape memory polymer perivascular wrap, J Biomed Mater Res. 2020;1-17.

* cited by examiner

| Score | 0 | 1 | 2 | 3 |
|---|---|---|---|---|
| Neovascularization | No blood vessels present | Vessels only at periphery | Vessels Present within interstices but not bridging | Vessels bridge implant in at least one focus |
| Fibrogenesis | Connective tissue bridges implant in multiple foci | Connective tissue bridges implant focally | Fibrosis at periphery beginning to invest interstices | Peripheral fibrosis only |
| Inflammation | Marked: Inflammation consists of a thick, circumferential cuff of neutrophils, multinucleated giant cells, histiocytes, lymphocytes, and plasma cells | Moderate: Inflammation consists of moderate, multifocal/segmented aggregation of multinucleated giant cells, histiocytes, lymphocytes, and plasma cells with fewer neutrophils | Mild: Inflammation consists of mild, multifocal/segmental aggregates of multinucleated giant cells, histiocytes, lymphocytes, and plasma cells with fewer neuthrophils; >50% of implant's circumference is affected | Minimal: Inflammation consists of mild, multifocal aggregates of multinucleated giant cells, histiocytes, lymphocytes, and plasma cells with infrequent neutrophils; <50% of implant's circumference is affected. |

Fig. 4

| Design | Diameter (μm) | Spacing (μm) | Void Area (mm² x 10²) | Porosity (%) |
|---|---|---|---|---|
| 1A | 273 ± 42 | 198 ± 68 | ~117 | ~30 |
| 2A | 658 ± 26 | 152 ± 46 | ~680 | ~60 |
| 3A | 1040 ± 25 | 124 ± 29 | ~1700 | ~72 |
| 1B | 320 ± 17 | 220 ± 35 | ~160 | ~32 |
| 2B | 671 ± 20 | 225 ± 51 | ~710 | ~51 |
| 3B | 1100 ± 29 | 243 ± 89 | ~1900 | ~61 |
| A | 273, 658, 1040 | 172 ± 54 (198, 152, 124) | ~117, 680, 1700 | 30, 60, 72 |
| B | 320, 671, 1100 | 224 ± 56 (220, 225, 243) | ~160, 710, 1900 | 32, 51, 61 |
| 1 | 293 ± 41 (273, 320) | 198, 220 | ~117, 160 | 30, 32 |
| 2 | 665 ± 24 (658, 671) | 152, 225 | ~680, 710 | 60, 51 |
| 3 | 1067 ± 35 (1040, 1100) | 124, 243 | ~1700, 1900 | 72, 61 |

| Design | Polymer | Pore Diameter (μm) | Spacing (μm) | Estimated Void Area (mm² x 10³) | Estimated Porosity (%) | E₀(37 °C) (MPa) | ε_max (%) | σ_max (MPa) |
|---|---|---|---|---|---|---|---|---|
| A | 68%PCL-32%ACPCL | 627 ± 50 | 148 ± 45 | ~620 | ~59 | 0.92 ± 0.26 | 69.0 ± 13 | 0.15 ± 0.03 |
| B | 68%PCL-32%ACPCL | 1180 ± 78 | 155 ± 52 | ~2200 | ~71 | 0.57 ± 0.25 | 106 ± 17 | 0.17 ± 0.02 |
| C | 68%PCL-32%ACPCL | 640 ± 71 | 223 ± 42 | ~640 | ~50 | 1.08 ± 0.30 | 78 ± 65 | 0.26 ± 0.06 |
| D | 68%PCL-32%ACPCL | 1140 ± 86 | 226 ± 58 | ~2000 | ~62 | 1.11 ± 0.12 | 76 ± 46 | 0.29 ± 0.08 |
| E | 68%PCL-32%ACPCL | Non/micro | N/A | N/A | N/A | 2.4 ± 0.86 | 52 ± 30 | 0.44 ± 0.09 |
| F | GORETEX (ePTFE) | 10 – 30 μm | N/A | N/A | N/A | 15.5 ± 1.8 | 139 ± 11 | 24.3 ± 1.8 |
| 150 | 68%PCL-32%ACPCL | 635, 1160 | 151 ± 50 | ~620, 2200 | ~59, 71 | 0.9, 0.57 | 69, 110 | 0.15 |
| 230 | 68%PCL-32%ACPCL | 635, 1160 | 229 ± 51 | ~640, 2000 | ~50, 62 | 1.1 | 78, 72 | 0.26 |
| 640 | 68%PCL-32%ACPCL | 635 ± 63 | 151, 229 | ~ 630 | ~59, 50 | 0.92, 1.1 | 69, 78 | 0.15, 0.26 |
| 1160 | 68%PCL-32%ACPCL | 1160 ± 64 | 151, 229 | ~2100 | ~71, 62 | 0.57, 1.1 | 110, 72 | 0.17, 0.26 |
| 0 – 30 | PCL-ACPCL, ePTFE | 0 – 30 | N/A | N/A | N/A | 2.4, 15.5 | 52, 139 | 0.44, 24.3 |

Fig. 8

|  | Pore Spacing | | | Pore Size | | |
|---|---|---|---|---|---|---|
| Design Compared | Mean Difference | Significant? | Adjusted P value | Mean Difference | Significant? | Adjusted P value |
| A vs. B | -7.172 | No | 0.2963 | -554.8 | Yes (****) | <0.0001 |
| A vs. C | -75.26 | Yes (****) | <0.0001 | -13.44 | No | 0.2759 |
| A vs. D | -87.99 | Yes (**) | <0.0001 | -513.9 | Yes (**) | <0.0001 |
| B vs. C | -68.09 | Yes (**) | <0.0001 | 541.4 | Yes (**) | <0.0001 |
| B vs. D | -80.82 | Yes (****) | <0.0001 | 40.95 | No | 0.0882 |
| C vs. D | -12.73 | No | 0.1027 | -500.4 | Yes (****) | <0.0001 |

Fig. 10

| | Peri-polymer localization | Other cells labeled |
|---|---|---|
| MMP3 | Monocyte-macrophages<br>Multinucleated giant cells<br>Endothelium | Dermal monocyte-macrophages<br>Neutrophils<br>Epidermal sebocytes<br>Striated myocytes |
| MMP9 | Monocyte-macrophages<br>Multinucleated giant cells | Dermal monocyte-macrophages<br>Neutrophils |
| MMP12 | Monocyte-macrophages<br>Multinucleated giant cells<br>Endothelium<br>Fibroblasts | Striated myocyes<br>Apocrine epithelial cells<br>Epidermal sebocytes<br>Dermal macrophages<br>Neutrophils<br>Epidermal keratinocytes |
| MMP13 | Monocyte-macrophages<br>Multinucleated giant cells | Dermal monocyte-macrophages<br>Neutrophils |
| MMP14 | Monocyte-macrophages<br>Multinucleated giant cells<br>Endothelium | Dermal monocyte-macrophages<br>Neutrophils<br>Epidermal sebocytes<br>Striated myocytes<br>Epidermal keratinocytes |

Fig. 14

| Pairwise Comparison | MMP-2 Δ[a] | p[b] | MMP-3 Δ | P | MMP-8 Δ | p | MMP-9 Δ | p | MMP-12 Δ | p | MMP-13 Δ | p | MMP-14 Δ | p |
|---|---|---|---|---|---|---|---|---|---|---|---|---|---|---|
| D vs. E | -0.701 | 0.891 | -1.37 | 0.743 | -1.12 | 0.753 | 0.795 | 0.909 | 3.45 | 0.420 | 1.64 | 0.693 | -1.92 | 0.304 |
| D vs. A | -0.0476 | 0.985 | 1.27 | 0.762 | 1.69 | 0.613 | 1.292 | 0.840 | 0.348 | 0.930 | 1.53 | 0.600 | -0.420 | 0.820 |
| E vs. F | 0.553 | 0.906 | 0.0459 | 0.991 | 0.947 | 0.769 | 0.288 | 0.918 | -0.167 | 0.976 | -0.130 | 0.974 | 0.992 | 0.430 |
| D vs. B | 0.502 | 0.828 | -1.10 | 0.792 | 1.49 | 0.650 | 1.54 | 0.802 | 0.434 | 0.887 | 2.04 | 0.498 | -0.693 | 0.717 |
| A vs. C | 0.0747 | 0.970 | -1.05 | 0.692 | -1.14 | 0.702 | 0.285 | 0.897 | 0.00768 | 0.998 | 0.306 | 0.873 | -0.241 | 0.872 |
| D vs. C | 0.0271 | 0.993 | 0.211 | 0.965 | 0.545 | 0.886 | 1.58 | 0.800 | 0.341 | 0.899 | 1.84 | 0.581 | -0.661 | 0.723 |
| A vs. B | 0.549 | 0.581 | -2.37 | 0.378 | -0.197 | 0.944 | 0.248 | 0.897 | 0.0855 | 0.982 | 0.512 | 0.594 | -0.274 | 0.860 |
| F vs. A | 0.101 | 0.896 | 2.59 | 0.497 | 1.86 | 0.537 | 0.208 | 0.914 | -2.93 | 0.546 | 0.0242 | 0.991 | 0.507 | 0.735 |
| D vs. F | -0.149 | 0.950 | -1.33 | 0.792 | -0.178 | 0.965 | 1.08 | 0.863 | 3.28 | 0.482 | 1.51 | 0.650 | -0.927 | 0.628 |
| Mean p | | 0.889 | | 0.735 | | 0.758 | | 0.871 | | 0.791 | | 0.717 | | 0.677 |
| Mean Δ | 0.300 | | 1.26 | | 1.02 | | 0.813 | | 1.227 | | 1.06 | | 0.737 | |
| Rank[c] | 7 | 7 | 2 | 5 | 4 | 4 | 6 | 5 | 5 | 2 | 2 | 3 | 6 | 1 |
| Mean Rank[d] | 7 | | 3.5 | | 4 | | 5.5 | | 3.5 | | 2.5 | | 3.5 | |
| A,B vs. C,D | -0.214 | 0.872 | 0.0227 | 0.994 | -1.32 | 0.460 | -0.627 | 0.833 | -0.221 | 0.909 | -0.868 | 0.632 | 0.226 | 0.845 |
| E,F vs. C,D | 0.438 | 0.848 | 1.45 | 0.515 | 0.924 | 0.656 | -0.152 | 0.965 | 3.19 | 0.176 | -0.653 | 0.783 | 1.09 | 0.334 |
| A,B vs. E,F | -0.652 | 0.735 | -1.43 | 0.525 | -2.24 | 0.212 | -0.476 | 0.722 | 2.97 | 0.226 | -0.215 | 0.899 | -0.867 | 0.371 |
| Mean p | | 0.818 | | 0.678 | | 0.443 | | 0.834 | | 0.437 | | 0.771 | | 0.517 |
| Mean Δ | 0.254 | | 1.319 | | 0.863 | | 0.673 | | 1.61 | | 0.923 | | 0.632 | |
| Rank | 7 | 6 | 2 | 4 | 4 | 2 | 5 | 7 | 1 | 1 | 5 | 3 | 6 | 3 |
| Mean Rank | 6.5 | | 3 | | 3 | | 6 | | 1 | | 4 | | 4.5 | |
| Total Rank[e] | 6.75 | | 3.25 | | 3.50 | | 5.75 | | 2.25 | | 3.25 | | 4.00 | |

[a] Δ = fold-change
[b] p = corrected p-value
[c] Rank = fold-change rank from highest (1) to lowest (7); p-value rank from lowest (1) to highest (7).
[d] Mean Rank = average of fold-change and p-value ranks
[e] Total Rank = average of Mean ranks for the 9 individual comparisons and 3 paired comparisons.

Fig. 15

| | Fold-change (p-value) | Protein | Gene | Protein ID | UniProtKB link | Biological Function |
|---|---|---|---|---|---|---|
| Upregulated by SMP Macroporous Scaffolds | 3.92 (0.107) | Phenylalanine – tRNA ligase beta subunit | Farsb | Q9WUA2 (SYFB_MOUSE) | | Protein heterotetramerization (part of cellular component biogenesis); phenylalanyl-tRNA aminoacylation (part of protein translation and gene expression) |
| | 3.08 (0.0826) | Macrophage metalloelastase | Mmp12 | P34960 (MMP12_MOUSE) | | Possible role in tissue injury and remodeling; possesses significant elastolytic activity. Positive regulator of epithelial cell proliferation involved in wound healing, gene expression, interferon-α secretion, and proteolysis |
| | 2.40 (0.1277) | Eukaryotic translation initiation factor 2 subunit 3 | Eif2s3x | P20029 (EIF2G_MOUSE) | | Early stages of protein synthesis, formation of translational preinitiation complex |
| | 2.37 (0.1377) | Lipoprotein lipase | Lpl | P11152 (LIPL_MOUSE) | | Enzyme on lumen surface of vascular endothelium involved in triglyceride metabolism; plays key role in the clearance, utilization, and storage of lipids; positive regulation of macrophage-derived foam cell differentiation |
| | 2.20 (0.0989) | Rab-related GTP-binding protein | Rage | Q9JHK7 (RRAGC_MOUSE) | | Binds GDP to form protein heterodimer complex that relocate mTORC1 to lysosome, a critical step in activating TOR signaling cascade |
| | 2.07 (0.1009) | 35 kDa erythrocyte membrane protein | Mpp1 | P70290 (EM55_MOUSE) | | Negative regulation of interleukin-1, apoptosis, cell migration, and membrane potential involved in neutrophil chemotaxis |
| | 1.85 (0.0983) | Interleukin C receptor antagonist protein | Ilra | P25085 (IL1RA_MOUSE) | | Regulates neutrophil chemotaxis by regulating autophagy polarity |
| | 1.83 (0.0603) | FK506-binding protein 15 | Fkbp15 | Q9Z0G8 (FKB15_MOUSE) | | Phagocytosis, lipid catabolism |
| | 1.80 (0.1046) | Phosphorylase b | Psd4 | Q9R0G7 (PSD4_MOUSE) | | Proteasome regulatory particle assembly, which is part of cellular component biogenesis |
| | 1.70 (0.1347) | 26S proteasome non-ATPase regulatory subunit 5 | Psmd5 | Q8BJY1 (PSMD5_MOUSE) | | Proteasome regulatory particle assembly, which is part of cellular component biogenesis |
| Downregulated | -1.80 (0.1365) | Calsequestrin-2 | Casq2 | O9R100 (CASQ2_MOUSE) | | Calcium-binding protein plays important role in initiating muscle contraction |
| | -1.86 (0.0898) | 60S ribosomal protein L39 | Rpl39 | P62892 (RL39_MOUSE) | | Liver metabolism protein; antibacterial humoral response; cytoplasmic translation |
| | -1.75 (0.1092) | Gelsolin | Gsn | Q3SX14 (GELS_BOVN) | | Actin filament severing, actin nucleation, barbed-end actin filament capping |

POLYMERIC VASCULAR GRAFTS WHICH INDUCE NEOVASCULARIZATION WITH MILD TO MINIMAL INFLAMMATION AND PROMOTION OF FIBROVASCULAR TISSUE

CROSS-REFERENCES TO RELATED APPLICATIONS

This application claims benefit of the following patent application(s) which is/are hereby incorporated by reference: U.S. Provisional Application No. 62/820,785 filed on Mar. 19, 2019.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to shape memory polymer devices. More particularly, this invention pertains to microporous shape memory polymer implants that can help induce neovascularization and tissue ingrowth, which may be important in mitigating neointimal hyperplasia when applied peridaventitially around veins.

Arteriovenous fistulas (AVFs) and arteriovenous grafts (AVGs) are the two preferred modes of vascular access in hemodialysis, as they are far less prone to bacteremia, sepsis, thrombosis, and central venous stenosis than are centralized venous catheters (CVCs). However, recent reports have found that approximately 30-40% of arteriovenous fistulas (AVF) fail to mature, and approximately 30% of those that do mature fail within the first year. Likewise, approximately 19% of AVGs undergo primary failure, with primary and secondary patency rates of just 30-50% and 55-70% at one year, respectively. In coronary artery bypass grafting (CABG), 10-20% of SVGs fail within the first year, and up to 50% within 10 years. Similarly, in the lower extremities of peripheral artery bypass grafts (PABGs), 30-50% fail within 5 years. Failures in AVFs and AVGs contribute to 5-year hemodialysis survival rates of just 42.0%, 30-day ESRD readmissions of 34.2%, and a substantial portion of the estimated costs absorbed by the Centers for Medicare and Medicaid Services (CMS) to treat hemodialysis access dysfunction.

The primary culprit of these failures is venous stenosis caused by neointimal hyperplasia (NH), as well as lack of positive remodeling in AVF maturation failure. Surgical trauma, an order of magnitude increase in pressure and flow, and other factors cause vascular smooth muscle cells (VSMCs) and myofibroblasts within the vein walls to migrate towards the intima and deposit extracellular matrix proteins to form a "neointima"; this neointima obstructs blood flow through the access site and requires further interventions or surgeries.

Systemic therapeutics to improve hemodialysis or vein graft patency have so far exhibited little to marginal benefit, putting the emphasis on therapeutic and/or device approaches that are localized to the access creation site, especially at, and proximal to, the venous anastomosis where the majority of AVF and AVG stenotic lesions typically occur. Perivascular approaches to improve maturation and patency of AVFs, AVGs, and vein bypass grafts for PABG and CABG have to date focused primarily on either promoting processes that are involved in outward remodeling (e.g. adventitial angiogenesis or elastin fragmentation) or attenuating vein wall tension and stresses with mechanical support.

Neointimal hyperplasia at the arteriovenous or graft-vein anastomosis is the main source of failure. Several studies have demonstrated the promise of external stents to reduce NH via promotion of neovascularization in the adventitia as well as through mechanical support. But, limited clinical success of these approaches so far may be attributed in part to inappropriate material selection (e.g. nondegradable, too stiff) and geometric design (e.g. pore size and spacing, diameter, length).

There remains a need for compositions and methods for treating vascular conditions that are relatively noninvasive, painless, and inexpensive. There also remains a need for such compositions and methods which provide better clinical success and decrease failure rates by increasing neovascularization, decreasing inflammation, and decreasing fibrogenesis.

BRIEF SUMMARY OF THE INVENTION

The present disclosure, in one or more embodiments, is drawn to an implantable tissue supporting device that may include a biodegradable polymeric scaffold capable of surrounding a tissue. The biodegradable polymeric scaffold may include at least one polymer. The at least one polymer may include at least one monomer that is crosslinkable. The biodegradable polymeric scaffold may be configured to have a melting temperature and be moldable from a first shape to a second shape by an external force when the melting temperature is met or exceeded. In some embodiments, the device may be mechanically compliant at from about 20 to about 50° C., and wherein the biodegradable polymeric scaffold has a pore size of about 500-750 µm and a pore spacing of about 220 µm to about 250 µm.

In some embodiments, the scaffold may have a pore size of about 600-700 µm, and a pore spacing of about 230 µm.

In some embodiments, the at least one monomer may be allyl functionalized and may include an allyl carboxylate group.

In some embodiments, the at least one monomer may include ε-caprolactone.

In some embodiments, the biodegradable polymeric scaffold may include a plurality of crosslinked polymers, the plurality of crosslinked polymers includes a poly(ε-caprolactone)-co-(α-allyl carboxylate ε-caprolactone) polymer. In some embodiments, the plurality of crosslinked polymers may include about 1 mol % to about 30 mol % of poly(ε-caprolactone).

In some embodiments, the device may have 50-100% shape fixity, and 50-100% shape recovery.

In some embodiments, the device is configured to include a Young's modulus at 37° C. of about 0.05-200 MPa.

In some embodiments, the tissue may be a vein or artery. In some embodiments, the device may be external to the vein or artery.

In some embodiments, the device may be configured such that it retains a shape to fit around said tissue when implanted. In some embodiments, the device may be external to a vascular graft anastomosis.

In some embodiments, the device may form a seamless and sutureless sheath.

In some embodiments, the device may include resilient radial expression in a manner that mimics the compliance properties of said tissue.

In some embodiments, the device may be deformable by at least one of stretching or bending along its length to conform to the shape of the tissue.

In some embodiments, the biodegradable polymeric scaffold may further include a shape memory polymer. In some embodiments, the shape memory polymer may have a melting temperature at or near body temperature.

In some embodiments, the biodegradable polymeric scaffold may include at least one monomer that is photocrosslinkable and further may include at least a second monomer that is not photocrosslinkable.

In some embodiments, the biodegradable polymeric scaffold may include at least one monomer that is allyl-functionalized and further may include at least one second monomer that is not allyl-functionalized.

In some embodiments, the biodegradable polymeric scaffold may be maintained at least 3 months after implantation.

BRIEF DESCRIPTION OF THE SEVERAL VIEWS OF THE DRAWINGS

FIG. 4 is a table of the histological scoring criterion.

FIG. 8 is a table with pore parameter characterizations for a porous scaffold embodiment of the present disclosure.

FIG. 10 is a statistical summary of pore parameter comparisons for a porous scaffold embodiment of the present disclosure.

FIG. 14 is a summary of observations from MMP IHC staining.

FIG. 15 is a pairwise comparison of MMP values from MMP IHC staining.

FIG. 16 is a summary of a proteomics analysis of embodiments of the present disclosure.

DETAILED DESCRIPTION OF THE INVENTION

Figure 1:
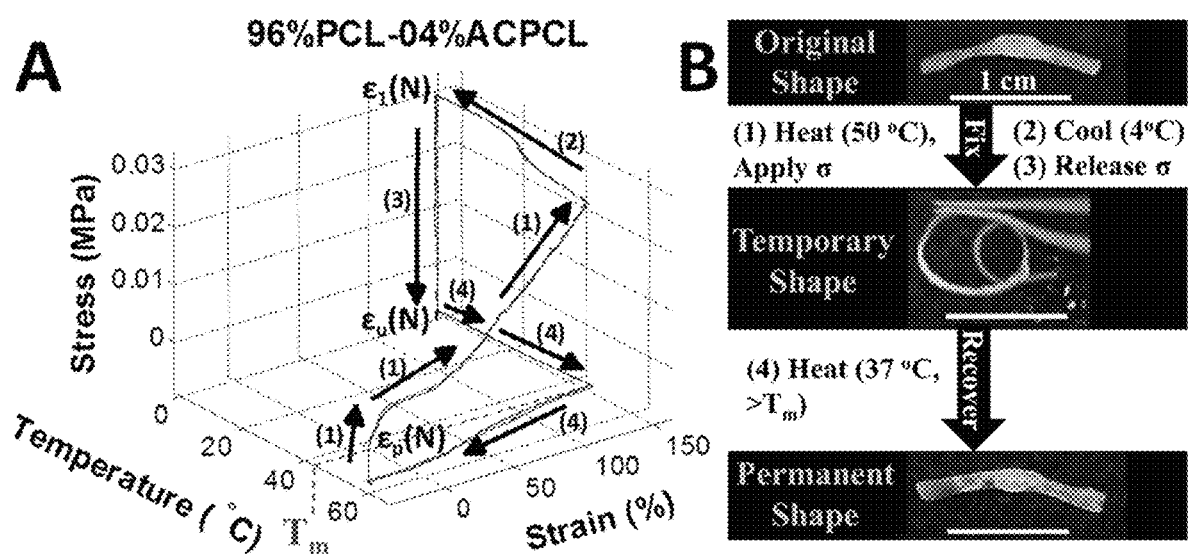
FIG. 1 demonstrates properties of one embodiment of a x % PCL-y % ACPCL polymer as disclosed herein.

The details of one or more embodiments of the presently disclosed subject matter are set forth in this document. Modifications to embodiments described in this document, and other embodiments, will be evident to those of ordinary skill in the art after a study of the information provided herein. The information provided in this document, and particularly the specific details and disclosures of the described embodiments, is provided primarily for clearness of understanding and no unnecessary limitations are to be understood therefrom. In case of conflict, the specification of this document, including definitions, if any, will control.

The presently disclosed subject matter includes compounds and methods for treating vascular conditions. Vascular conditions can often lead to severe complications or even death. Such vascular conditions include but are not limited to, hemorrhages, aneurysms, occlusions, and ischemic tissue. Vascular conditions also present unique treatment challenges. This may be particularly so when treating vessels that are small or difficult to access. For instance, traditional surgical treatment techniques may be invasive to surrounding tissue and may be prohibitively costly, can result in a high amount of pain, and can require a lengthy recovery.

In this regard, thermo-responsive shape memory polymers (SMPs) have drawn extensive interest in a wide range of applications, including biomedical, aerospace, self-healing, and textile applications. Such SMPs may recover their original shape after being programmed into a distinct temporary shape.

One embodiment of the present invention may include a mechanically compliant, moldable, porous, shape memory external support that may be custom fit around a vascular graft anastomosis to prevent neointimal formation. This embodiment may also provide localized, sustained delivery of therapeutics with anti-neointimal effects. In some embodiments, the presently disclosed compounds may include allyl-functionalized SMPs that can be crosslinked via pendant allyl groups. In some embodiments, the presently disclosed materials may be comprised of SMPs, and in certain embodiments may include thermo-responsive SMPs that actuate at or near physiological temperature (e.g., about 37° C.). The present materials may be advantageous over the prior art because they can be relatively high in elastic recovery, easy to manufacture and program, low cost, compatible with vasculature, tunable, and/or biodegradable. Thus, embodiments of the present materials that possess some or all of these features may be advantageous for manufacturing simple and minimally invasive implantable devices for various biomedical applications.

One embodiment of the present disclosure may include an implantable tissue supporting device. In some embodiments, the implantable tissue supporting device may be disposed around a venous anastomosis to prevent neointimal formation and associated AVG failure via promotion of outward remodeling, instead of inward remodeling. In some embodiments, the implantable tissue supporting device may provide localized, sustained delivery of therapeutics. It will be understood that the term "external support" covers a variety of devices, including an implantable tissue supporting device, among others.

One embodiment of the present disclosure may be an external support or an implantable tissue supporting device, in the form of a porous biodegradable polymeric scaffold that surrounds a tissue. In some embodiments, the polymeric scaffold may include at least one polymer, wherein the polymer may further include at least one monomer that is crosslinkable. In some embodiments, the polymer may include at least one shape memory polymer. In some embodiments, the polymer may include both at least one monomer that is crosslinkable and at least one shape memory polymer. In some embodiments, the support device may be capable of transforming between an original shape and an implanted shape; and wherein the device may be mechanically compliant at from about 20° C. to about 50° C. In some embodiments, the polymeric scaffold may be porous and have a pore size and pore spacing that induces favorable cellular responses.

In some embodiments, the polymeric scaffold of an external support may include a polymer having at least a first monomer and at least a second monomer. The first monomer may be allyl functionalized and may include an allyl carboxylate group. Additionally, the first monomer, the second monomer, or both may be an ester. In other embodiments, the first monomer, the second monomer, or both include ε-caprolactone (CL). In some embodiments, the polymeric scaffold may include a plurality of crosslinked polymers. The plurality of crosslinked polymers may include a poly (ε-caprolactone)-co-(α-allyl carboxylate ε-caprolactone) polymer (PCL-ACPCL). In some embodiments, the plurality of crosslinked polymers may include a first monomer including PCL and a second monomer of ACPCL. In some embodiments, the first monomer may be ACPCL and the second monomer may be PCL. In some embodiments, the plurality of crosslinked polymers may include about 1 mol % to about 30 mol % of the first monomer. In other embodiments, the plurality of crosslinked polymers may include a shape transition temperature from about 20° C. to about 50° C.

The ratio of the first monomer to the second monomer may vary depending on the embodiment and the melting temperature that is preferred. In some embodiments the compound is comprised of about 1 mol %, 5 mol %, 10 mol %, 15 mol %, 20 mol %, 25 mol %, 30 mol %, 35 mol %, 40 mol %, 45 mol %, or 50 mol % of the first monomer. In other embodiments the compound is comprised of about 1 mol % to about 50 mol % of the first monomer, about 1 mol % to about 30 mol % of the first monomer, or about 1 mol % to about 15 mol % of the first monomer. In such embodiments the remainder of the polymer may be comprised of the second monomer.

In some embodiments, the first monomer, the second monomer, or both include an ester. The term "ester" as used herein is represented by a formula $R_1OC(O)R_2$ or $R_1C(O)OR_2$, wherein $R_1$ and $R_2$ can be independently selected from, but are not limited to, an optionally substituted alkyl, alkenyl, alkynyl, or the like. The term ester is inclusive of "polyester," or compounds comprising two or more ester groups.

In some embodiments the first monomer that is allyl functionalized includes an allyl carboxylate group. In such embodiments, the monomer may include a carboxylate group that is then functionalized with an allyl group, or the monomer may be functionalized with the carboxylate allyl group.

In some embodiments the first monomer, the second monomer, or both may include ε-caprolactone (CL) and/or derivatives thereof. For instance, the first monomer including ε-caprolactone can include an α-allyl carboxylate ε-caprolactone (ACCL) monomer. In some embodiments the compounds are based on polycaprolactone (PCL) because PCL has desirable properties for vascular applications, including biocompatibility, suitable rates of biodegradability, and mechanical compliance. Thus the first monomer may include ACPCL. Similarly, the first monomer may include poly(ε-caprolactone) (PCL) alone.

Some embodiments of the compound may include a block copolymer. A "block copolymer" refers to a structure comprising one or more sub-combination of constitutional or monomeric units. In some embodiments, constitutional units are derived via additional processes from one or more polymerizable monomers. There is no limitation on the number of blocks, and in each block the constitutional units may be disposed in a purely random, an alternating random, a regular alternating, a regular block, or a random block configuration unless expressly stated to be otherwise.

As mentioned above, the present compounds can include allyl functionalized monomers that are crosslinkable. The terms "crosslinkable," "crosslink," and the like are used here to refer to an attachment of one portion of a polymer chain to a portion of the same polymer chain or a portion of another polymer chain by chemical bonds that join certain atom(s) of the polymer chain(s). Exemplary chemical bonds that can form crosslinks include covalent bonds and hydrogen bonds as well as hydrophobic, hydrophilic, ionic, or electrostatic interactions. In some instances, covalently crosslinked SMP materials may exhibit superior shape memory properties and thermal stability when compared to SMP materials crosslinked by non-covalent bonds.

Cross-linking may be effected naturally or artificially. For instance, in some embodiments, the first monomer may be photocrosslinkable, where the term "photocrosslink" and the like may be understood and used herein to refer to crosslinks that are formed upon being exposed to electromagnetic radiation, such as visible light and/or ultraviolet radiation. In some embodiments, photocrosslinks can be formed by exposure to ultraviolet light having a wavelength of about 100 nm to about 300 nm. The terms "crosslink" and the like as used herein can be inclusive of the terms "photocrosslink" and the like.

In some embodiments, the allyl-functionalized monomer includes a pendant allyl-including group (e.g. carboxylate allyl group) that can crosslink. In some embodiments the allyl-including group may photocrosslink to another allyl-including group of the same compound or another compound.

In some embodiments the present compounds are biocompatible. Certain embodiments of the present compounds and external supports may be more biocompatible with endothelial cells (ECs) than 100% PCL, as indicated by higher levels of long-term cell viability and healthy cell morphologies. The term "biocompatible" as used herein may be understood to describe a characteristic of substances that do not typically induce undesirable or adverse side effects when administered in vivo. For example, biocompatible substances may not induce side effects such as significant inflammation and/or acute rejection. It should be understood by one of skill in the art that "biocompatibility" is a relative term, and some side effects can be expected even for some substances that are biocompatible. In some embodiments, a biocompatible substance may not induce irreversible side effects, and in some embodiments a substance may be biocompatible if it does not induce long term side effects. One test to determine the biocompatibility of a substance is to measure whether cells die upon being exposed to a material in vitro. For instance, a biocompatible compound or material may cause less than about 30%, 20%, 10%, or 5% cell death.

Additionally, or alternatively, some embodiments of the present compounds may be biodegradable. The term "biodegradable" as used herein may be understood to describe a characteristic of substances that may degrade under physiological conditions to form a product that may be metabolized or excreted without damage to the subject. In certain embodiments, the product may be metabolized or excreted without permanent damage to the subject. Biodegradable substances may also include substances that may be broken down within cells. Degradation may occur by hydrolysis, oxidation, enzymatic processes, phagocytosis, other processes, and combinations thereof. Degradation rates for substances can vary, and may be on the order of hours, days, weeks, months, or years, depending on the material composition and its chemical and physical properties.

The presently disclosed subject matter also includes shape memory polymer materials comprised of any of the presently disclosed compounds. In some instances, the materials may be utilized to form external support devices, such as an implantable tissue support device for deployment around a tissue. In some embodiments, the tissue may be a vein or artery. In some embodiments, the external device may be deployed external to the tissue. In some embodiments, the tissue may be a vascular graft anastomosis, and the device may be deployed external to the anastomosis. Exemplary external supports may include a plurality of crosslinked polymers, the polymers including a first monomer that is allyl functionalized and crosslinkable and a second monomer that not crosslinkable, and the external support may be capable of transforming between a temporary shape and an original shape.

The term "implanted shape" as used herein may be understood to refer to a shape that has been given to a material by exerting a force on the material and/or exposing the material to certain temperatures (i.e., programming step). While the material may retain its temporary shape for any length of time, the shape may be referred to as being temporary because the shape may exist only when external force is exerted on the material. Furthermore, in some embodiments the materials may lose their temporary shape when exposed to a temperature above a melting temperature of the material.

The term "original shape" may be understood to refer to a shape of the material when the polymers of the material are in their native, pre-implanted, unstrained state. Once a material is in its original shape, a material may generally retain the original shape unless an external force or the like is applied to the material. Some embodiments of materials may revert to and/or retain an original shape when exposed in a physically unstressed state to a temperature above a melting temperature of the material (i.e., recovery step). Crosslinks between the plurality of polymers that comprise the materials, either chemical or physical in nature, may help prevent irreversible, plastic deformation during programming and recovery steps.

There are no particular limitations on what shapes can be assumed by the material in its temporary shape or its original shape. In some embodiments, the temporary shape may be selected from a thread, a sheet, tubular shape, a shape corresponding to a blood vessel, a vascular patch, a vascular bypass graft, a vascular stent, a vascular graft anastomosis, and combinations thereof. Likewise, in some embodiments the original shape may be selected from a thread, a sheet, tubular shape, a shape corresponding to a blood vessel, a vascular patch, a vascular bypass graft, a vascular stent, a vascular graft anastomosis and combinations thereof.

Embodiments of the present materials may be categorized as thermomechanical SMPs, whereby the polymers may exhibit a transition from a temporary shape to an original shape when transitioning above and/or below a melting temperature of the compounds. For instance, a material may initially have an original shape, and a temporary shape can be induced by heating the material above its melting temperature while exerting a force on the material that molds or bends the material into a desired temporary shape. The material may then retain its temporary shape if it is cooled to a temperature below the melting point of the material while holding the material in the temporary shape, and the material may substantially retain this temporary shape so long as it is kept at a temperature below the melting temperature of the material. Subsequently, the material may revert to its original shape by heating the material to a temperature above its melting temperature.

The present compounds and materials may include a wide range of melting temperatures. In some embodiments, the compounds and materials may include a melting temperature of about 20° C. to about 50° C., including melting temperatures of about 20° C., 25° C., 30° C., 35° C., 40° C., 45° C., and 50° C. In some embodiments the compounds and materials may include a melting temperature that is at or substantially near physiological temperature (e.g., about 37° C.) so that the materials may experience a switch-like shape transition when implanted into a subject. The present materials may also include relatively high elastic recovery. In some embodiments, the present materials may include a strain recovery rate (Rr) and/or strain fixity rate (Rf) of 90% or more, and in some embodiments Rr and/or Rf can independently be about 91%, 92%, 93%, 94%, 95%, 96%, 97%, 98%, or 99% or more. The present materials may also possess qualities that make them similar to, and therefore appropriate for, use in conjunction with blood vessels. For instance, some embodiments of materials may include compliant and ductile qualities that may be suitable for use with vasculature. Some embodiments may also include elastic moduli of about 1.0 to about 200.0 MPa at 37° C., which may be suitable for certain vascular applications.

Embodiments of the present disclosure that include a PCL-ACPCL based SMPs may exhibit a physical property of melting at or near body temperature. In one embodiment, a custom-fittable external support may include a porous surface that is slowly-biodegradable. In another embodiment, the PCL-ACPCL SMP may be moldable at or near body temperature. As the SMP melts, transitioning from an elastic to a viscoelastic state, the external support may mold itself to the specific geometry of a venous anastomosis or a vascular graft anastomosis. Due to the porous properties, the external support may promote more uniform outward vein remodeling and may minimize asymmetric wall thickening that may cause turbulent irregular flow and subsequent neointimal hyperplasia. In some embodiments, the external support may also enhance vein surface area coverage, which may lead to better dissipation of heightened wall tensions and stresses in the arteriovenous environment as compared to products of the prior art.

Some embodiments of the present disclosure may include external support devices using materials that are slowly biodegradable in vivo. It will be understood that slowly biodegradable will generally include an external support that will maintain at least a portion of the support in vivo for at least 1 year. In some embodiments, the external support may degrade over a period of 2 years or more. It will also be understood that some embodiments may be biodegradable at a faster rate but should generally maintain a portion of the support structure for at least 3 months. The 3-month time period may allow for the external support to ensure sufficient mechanical support for the critical remodeling period that may generally last 3 months. In some embodiments, the external support may be completely biodegradable, which may include the support being fully resorbable. Biodegradability may help to mitigate risk of infection, chronic inflammation, and neointimal hyperplasia-induced compliance mismatches.

In some embodiments, different portions of the external support may have different biodegradability properties and/or rates. In one embodiment, one portion of the external support may degrade at a more rapid rate than another portion. In one embodiment, all portions may be biodegradable, but may degrade at different rates which provide different functions for the support. In some embodiments, one portion of the external support may be biodegradable while another portion my be non-biodegradable.

As indicated above, embodiments of the present invention may surround a tissue, such as a vein and/or artery. In some embodiments, the device may be external to the vein or artery. In some preferred embodiments, the device may be external to a vascular graft anastomosis.

Once implanted, embodiments of the present disclosure may form a seamless and sutureless sheath. The sheath may be mesh or netting. Additionally, once implanted, some embodiments may include physical properties that demonstrate resilient radial expression in a manner that mimics the compliance properties of the tissue. The embodiments may be deformable by at least one of stretching or bending along its length to conform to the shape of the tissue.

Figure 2:
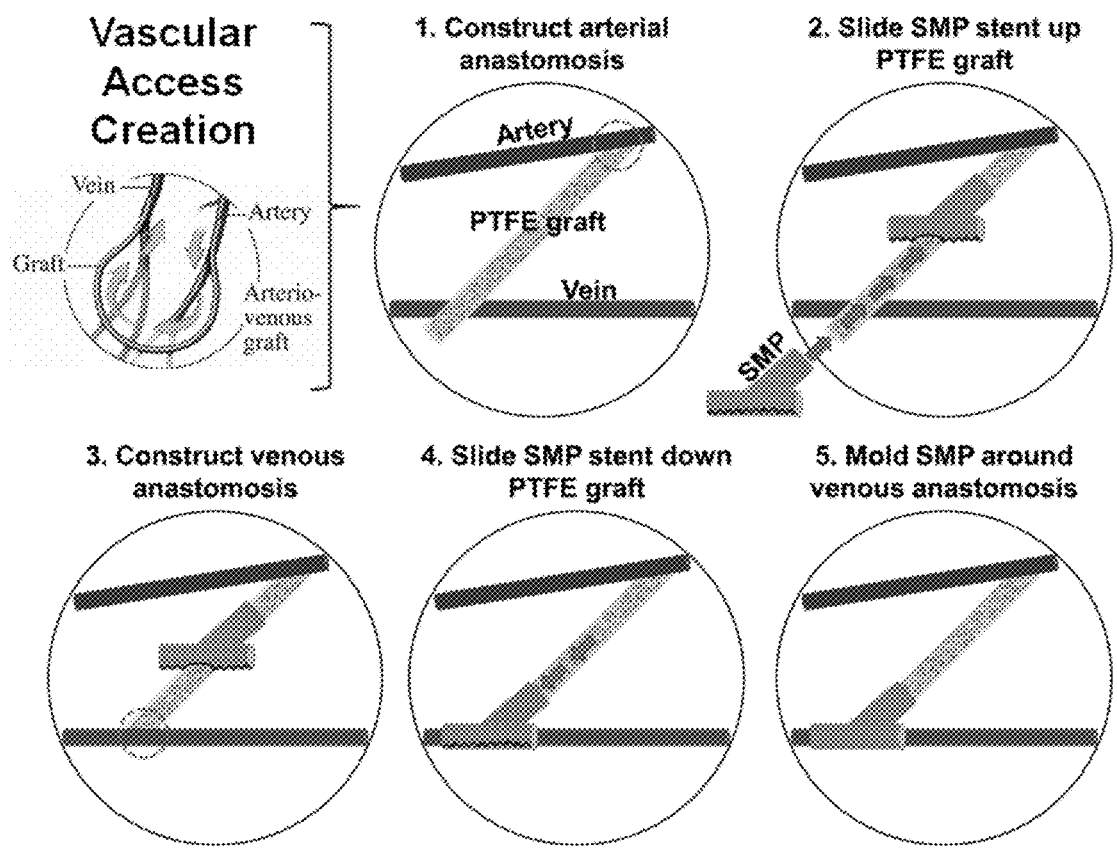
FIG. 2 illustrates a scheme for vascular access creation and molding of an embodiment of the present disclosure.

In some embodiments, the custom-fit of the device at vascular access operating temperatures (e.g., about 28-37° C.) may be possible due to the chemical properties from copolymerizing ε-caprolactone (CL) with α-allyl carboxylate-ε-caprolactone (ACCL). This copolymer may produce a polymer library with Tm's ranging from at least 28-43° C. and may further include exceptional shape memory properties. (FIG. 1). Given the shape memory capabilities around 37° C., the geometry of external supports may be custom tailored during implantation with relative ease to fit the asymmetric distal anastomosis. (FIG. 2).

Figure 3:
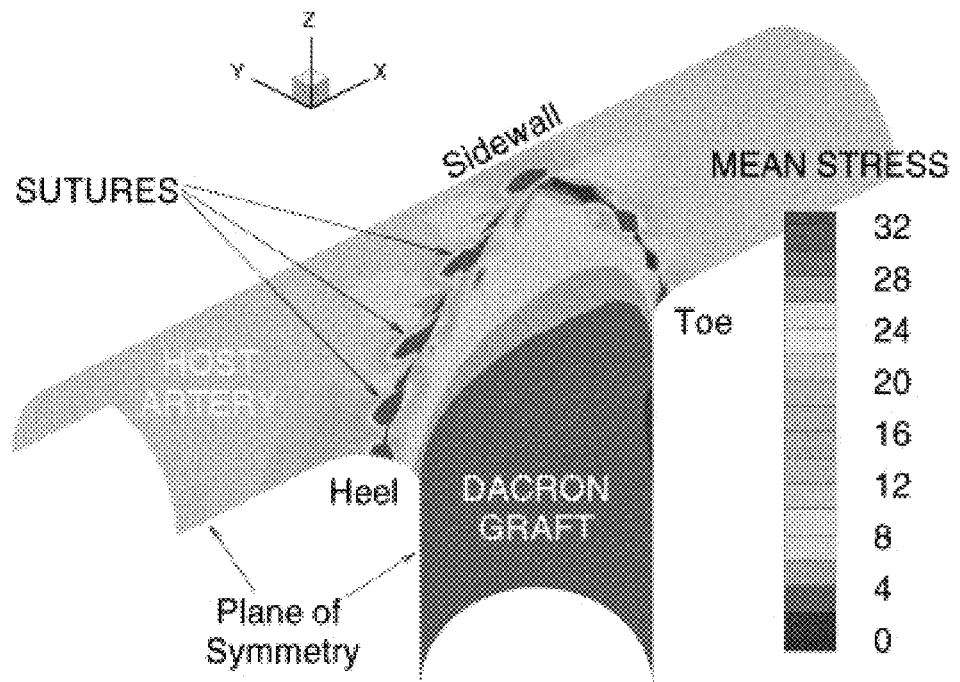
FIG. 3 illustrates an embodiment of the present disclosure and demonstrates mean stress distribution at the end-to-side Dacron graft-artery anastomosis.

Embodiments with this copolymerization chemical makeup may also enable fine-tuning of thermomechanical properties such that SMP external supports may be fabricated with artery-mimetic mechanical properties. Such properties may be important because compliance mismatch between a vein and a synthetic graft or artery is one factor involved in neointimal formation. For example, a 68% decrease in mechanical compliance from a blood vessel to a graft, equivalent to transitioning from an artery to Dacron, may result in a 40% increase in mean anastomotic stress along suture lines and subsequent neointimal formation in an end-to-side geometry. (FIG. 3).

In addition to the chemical properties of the device, the macromolecular properties of the device may also be used to impart important physical characteristics and functions. In particular, embodiments having a porous surface may be useful in fostering adventitial microvessel formation.

In some embodiments, the porous surface may be dictated by certain pore parameters, such as pore size, pore spacing, and overall porosity. These features may influence angiogenic responses induced by polymeric scaffold implantation. The pore parameters of this disclosure may affect the surface area-to-volume ratio and topology and may play a role in the extent and type of inflammatory reactions observed in vivo. Prior art products have had difficulty in incorporating products that are pro-angiogenic, pro-outward remodeling, or anti-inflammatory, immunosuppressant therapeutics to similar devices as disclosed herein. None have recognized the potential for modifying the pore parameters of a porous external support device to influence angiogenic, outward remodeling, neoadventitial growth, and inflammatory reactions in vivo.

Some embodiments of the present disclosure may include an implantable tissue supporting device, in the form of a porous biodegradable polymeric scaffold that surrounds a tissue. In some embodiments, the polymeric scaffold may include at least one polymer, wherein the polymer may further include at least one monomer that is crosslinkable and/or at least one shape memory polymer. In some embodiments, the support device may be capable of transforming between an original shape and an implanted shape; and wherein the device is mechanically compliant at from about 20° C. to about 50° C. In some embodiments, the polymeric scaffold may be porous and have a pore size and pore spacing that induces favorable cellular responses.

Figures 5, 6:
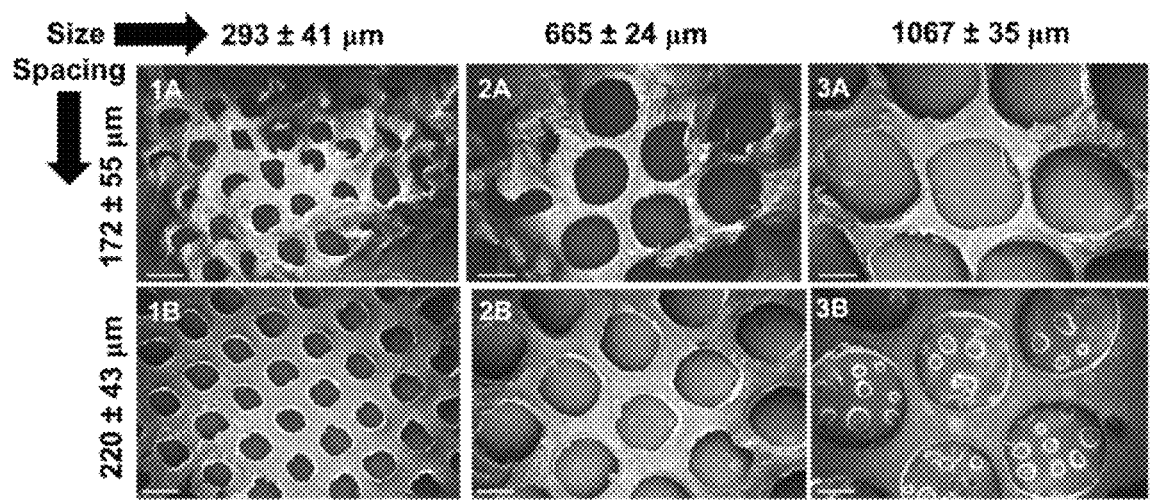
FIG. 5 is a group of SEM micrographs of a porous scaffold embodiment of the present disclosure.
FIG. 6 is a table with pore parameter characterizations for a porous scaffold embodiment of the present disclosure.
Figure 7:
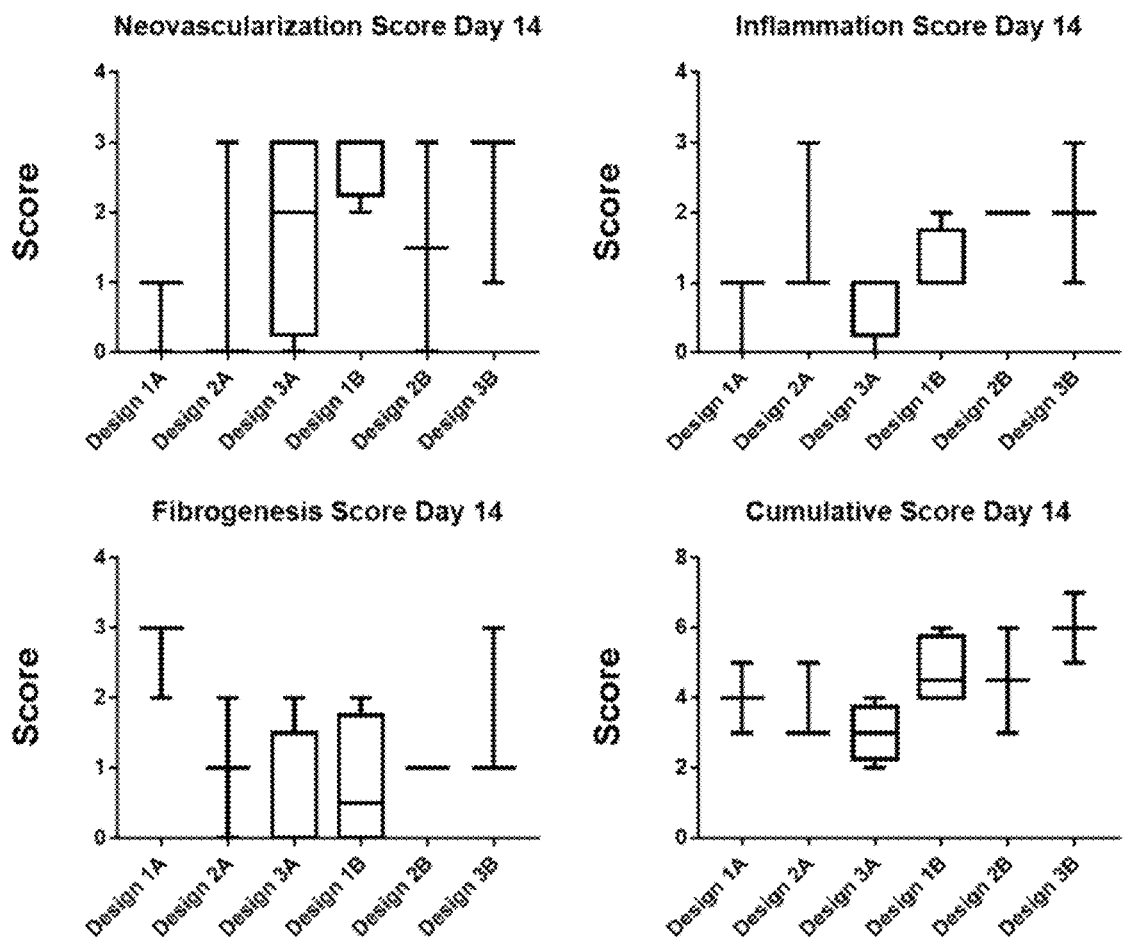
FIG. 7 is a graph of histological scoring results for a porous scaffold embodiment of the present disclosure.
Figure 9:
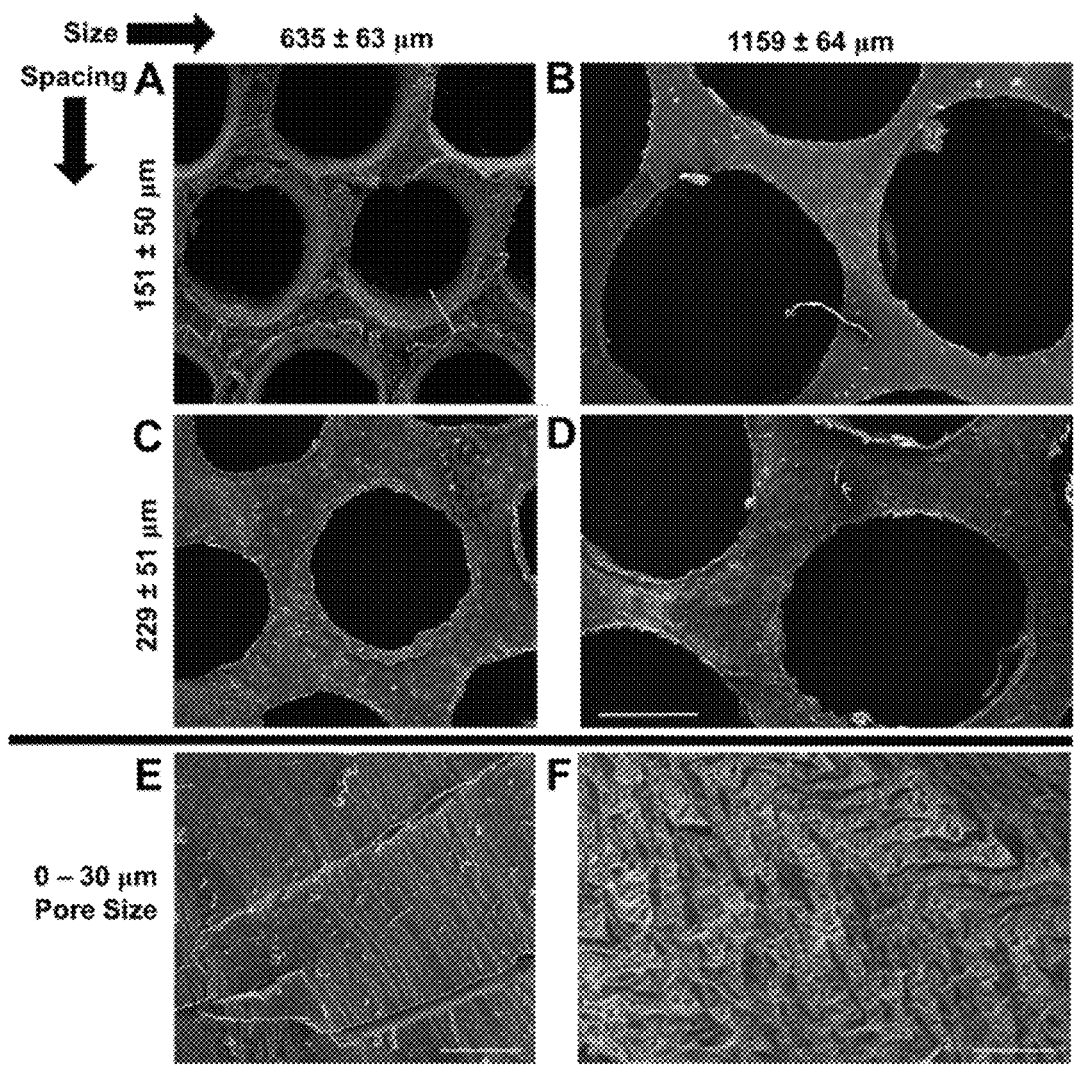
FIG. 9 is a group of SEM micrographs of a porous scaffold embodiment of the present disclosure in comparison to non porous polymers and microporous polymers.

In some embodiments, the porous biodegradable polymer scaffold may include a porous surface with pore spacing of between 100 to 400 microns. In some embodiments, the pores may be spaced apart between 200 and 300 microns. In some embodiments, the pores may be spaced between 220 and 250 microns. In some embodiments, the pores may be spaced approximately 220 microns apart. (FIG. 5). In some embodiments, the pores may be spaced approximately 230 microns apart. (FIG. 9). Embodiments including porous external support devices may elicit a more favorable tissue response by increasing neovascularization and/or decreasing inflammation and fibrosis in comparison to microporous structures and closer-spaced pores in general.

In some embodiments, the porous biodegradable polymer scaffold may include a porous surface with pore sizes between 500 microns and 750 microns. In some embodiments, the pore size may be between 600 and 700 microns. In some embodiments, the pore size may be about 630 microns, 635 microns, 640 microns, 645 microns, 650 microns, 655 microns, 660 microns, 665 microns, 670 microns, or 675 microns.

The presently disclosed subject matter further includes methods for treating a vascular condition. In some embodiments the method may include administering an external support device in a temporary shape to a subject in need thereof, the device comprising a plurality of crosslinked polymers that include a first monomer that is allyl-functionalized and crosslinkable and a second monomer that not crosslinkable. The embodied methods may further comprise a step of allowing the external support device to transform from the temporary shape to an original shape. The transformation from a temporary shape to an original shape may be initiated by heating the device above the melting point of the plurality of polymers, and in some embodiments the heating may be done passively from heat that is emitted from the subject.

The step of administering the external support device may include molding the external support device to a blood vessel of interest, to an artery, to a vein, or to a vascular graft anastomosis. As used herein, the term "mold" and the like refers to the placement and shaping of the external support to a blood vessel and exerting a force to the support such that it forms a sheath around the blood vessel. In some embodiments, molding may refer to wrapping a sheet-like external support completely around a blood vessel.

The terms "treatment" or "treating" as used herein may be understood to refer to the medical management of a subject with the intent to cure, ameliorate, stabilize, or prevent a disease or pathological condition. The term "condition" may be understood to be inclusive of diseases, disorders, and the like. "Treatment" may be understood to include active treatment, that is, treatment directed specifically toward the improvement of a condition, and also includes causal treatment, that is, treatment directed toward removal of the cause of the associated disease, pathological condition, or disorder. In addition, "treatment" may be understood to include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Furthermore, the terms "subject" or "subject in need thereof" may be understood to refer to a target of administration, which optionally displays symptoms related to a particular disease, pathological condition, disorder, or the like. The "subject" of the herein disclosed methods may be a vertebrate, such as a mammal, a fish, a bird, a reptile, or an amphibian. Thus, the subject of the herein disclosed methods may be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A "patient" may be understood to refer to a subject afflicted with a disease or disorder. The term "subject" may include human and veterinary subjects.

In some embodiments, the method may include providing an implantable tissue supporting device in an original shape wherein the implantable tissue supporting device is not implanted in a subject. The device may comprise a biodegradable polymeric scaffold wherein the scaffold may include a plurality of crosslinked polymers that include a first monomer that is allyl-functionalized and crosslinkable and a second monomer that not crosslinkable. The scaffold of the device may be porous and have a pore size of about 600-750 µm and a pore spacing of about 220 µm or more. In some embodiments, the scaffold may include a pore size of about 500-700 µm, and a pore spacing of about 220 to about 250 µm. In some embodiments, the pore size and spacing may be the same as disclosed previously.

Once the implantable tissue supporting device is provided, it may be administered to a subject wherein the device is positioned in the subject causing the polymers of the device to reach and/or surpass the melting temperature. The implantable tissue supporting device may then be manipulated to surround an artery, vein, or venous graft anastomosis. The step of manipulating the device may include molding the device to custom-fit around the specific artery, vein, or venous graft anastomosis of the subject. The implantable tissue supporting device may be retained in its external position until it degrades. In some embodiments, the device may degrade entirely. In some embodiments, a portion of the device may not degrade and may remain as an implant.

The presently disclosed compounds and external supports present several advantages for methods of treating vascular conditions. First, the external supports may include an original or temporary shape that provides for a custom-fit device that avoids neointimal hyperplasia and produces advantageous cellular responses over the prior art. The ability to customize the shape of the device also makes it suitable for unusual vasculature, such as branched arteries, as well as for treating other non-vascular conditions. The ability to customize the shape also permits the present compositions and external support devices to achieve robust and facile surgical placement via minimally invasive techniques.

Once implanted, the present external supports may offer mechanical compliance that withstands blood vessel pulsation similar to an artery. Further still, embodiments of the present disclosure may be biocompatible and, optionally, may exhibit biodegradable characteristics that are sufficiently slow to permit healing of the vasculature. The present embodiments may also have a porosity that promotes microvascular growth to repair damaged vessel tissue. The present compositions, devices, and methods may therefore provide treatments that are easily implemented, cost effective, and less invasive to the subject.

EXAMPLES

The presently disclosed subject matter is further illustrated by the following specific but non-limiting examples. The following examples may include compilations of data that are representative of data gathered at various times during the course of development and experimentation related to the presently disclosed subject matter.

Example 1

This example describes the preparation of SMP films with crosslinked x % PCL-y % ACPCL. The crosslinked x % PCL-y % ACPCL films of uniform thickness (0.2-0.3 mm) were produced from a 10 wt % polymer solution containing 3 wt % 2,2-dimethoxy-2-phenylacetophenone via a thin film applicator (Precision Gage & Tool, Co., Dayton, Ohio) and 365 nm irradiation (4.89 J cm-2, 18.1 mW cm-2) with a Novacure 2100 Spot Curing System (Exfo Photonic Solutions, Inc., Mississauga, Ontario, Canada). After drying, samples were incubated in DCM for 2 days to determine gel content. To induce pores, 8×4 mm spherical pore arrays spaced evenly apart were drawn in CAD designs and cut using a Laser Engraver (KERN Laser Systems, Wadena, Minn.) at a power of 1.5 W, speed of 0.08 in/sec, and frequency of 500 Hz. Films were then thoroughly washed in ethanol.

Example 2

This Example describes the pore parameter characterization and influence on tissue response based on SMP embodiments as prepared in Example 1. SMP scaffolds of different pore sizes and spacing were prepared for implantation. (FIG. 5, FIG. 6). Pore size and spacing were characterized by scanning electron microscopy (SEM). Samples were mounted onto aluminum studs covered by carbon adhesive, coated with gold and palladium, and imaged on a Quanta 250 Environmental SEM (Thermo Fisher Scientific, Waltham, Mass.). Pore diameter and spacing were determined by calculating the mean±SD from individual measurements on ImageJ software (NIH, Bethesda, Md.). Porosity was calculated as the ratio of void area:total area by assuming that pore diameter does not vary as a function of height and assuming that pores are exactly equidistant from one another:

$$\text{Porosity (\%)} = \frac{2\pi \left(\frac{Diameter_{pore}}{2}\right)^2}{\sqrt{3}\,(Diameter_{pore} + Spacing_{pore})^2}$$

Neovascularization, inflammation, and fibrogenesis were evaluated for each design at 14 days post-implantation by a blinded, board-certified veterinary pathologist at Vanderbilt University based on an established scoring criterion as described in FIG. 4. A cumulative score was calculated for samples of each design by summing the scores for each of the three categories. (FIG. 4—Appx. A) PCL-ACPCL scaffolds with higher pore spacing (~230 microns) elicited more favorable tissue responses of more neovascularization, less inflammation, and less fibrosis in comparison to closer-spaced pores (~150 microns).

Example 3

This Example describes an external support utilized to determine the pore parameter characterization and influence on tissue response based on embodiments of the present disclosure. SMP scaffolds of different pore sizes and spacing were prepared for implantation. In this example, the SMP comprised 68% PCL-32% ACPCL which were paired for pore size and spacing. In addition, a microporous and nonporous control were prepared. The nonporous control comprised non laser ablated 68% PCL-32% ACPCL. The microporous control comprised a ~6 mm×8 mm×0.62 mm piece of commercially-available Standard Wall GORE-TEX® tubing comprised of expanded polytetrafluoroethylene (ePTFE) and is reported to have micropores of 10-30 microns in diameter. Pore size and spacing were characterized by scanning electron microscopy (SEM) as described above. (FIG. 5, FIG. 9).

To determine mechanical and shape memory properties of the SMP films, pore designs (~12 mm×~6 mm×~0.4 mm) and nonporous controls (~12 mm×~2 mm×~0.4 mm) were loaded on a tensile clamp of a dynamic mechanical analyzer (TA Instruments Q2000). The tensile mechanical properties were determined isothermally at 37° C. using a stress ramp of 0.1 MPa sec$^{-1}$. The initial slope of the stress vs. strain curve was used to determine the modulus at 37° C., $E_m(37°$ C.). (FIG. 10). The Young's modulus of both nonporous (2.4±0.86) and porous (mean=0.57-1.11 MPa) 68% PCL-32% ACPCL designs may be close to the average physiological modulus of healthy human coronary arteries (1.48 MPa), suggesting suitability of the designs for vascular and soft tissue applications from a mechanical perspective. Ablating pores in the crosslinked polymer designs resulted in significant decreases in $E_m(37°$ C.) and $\sigma_{max}$ for all of the designs (p<0.003). Decreasing the spacing of the pores from 229±51 μm (C,D) to 151±51 μm (A,B) further reduced both $E_m(37°$ C.) and $\sigma_{max}$. Poor spacing may be a better predictor of mechanical properties than pore size.

Figure 11:
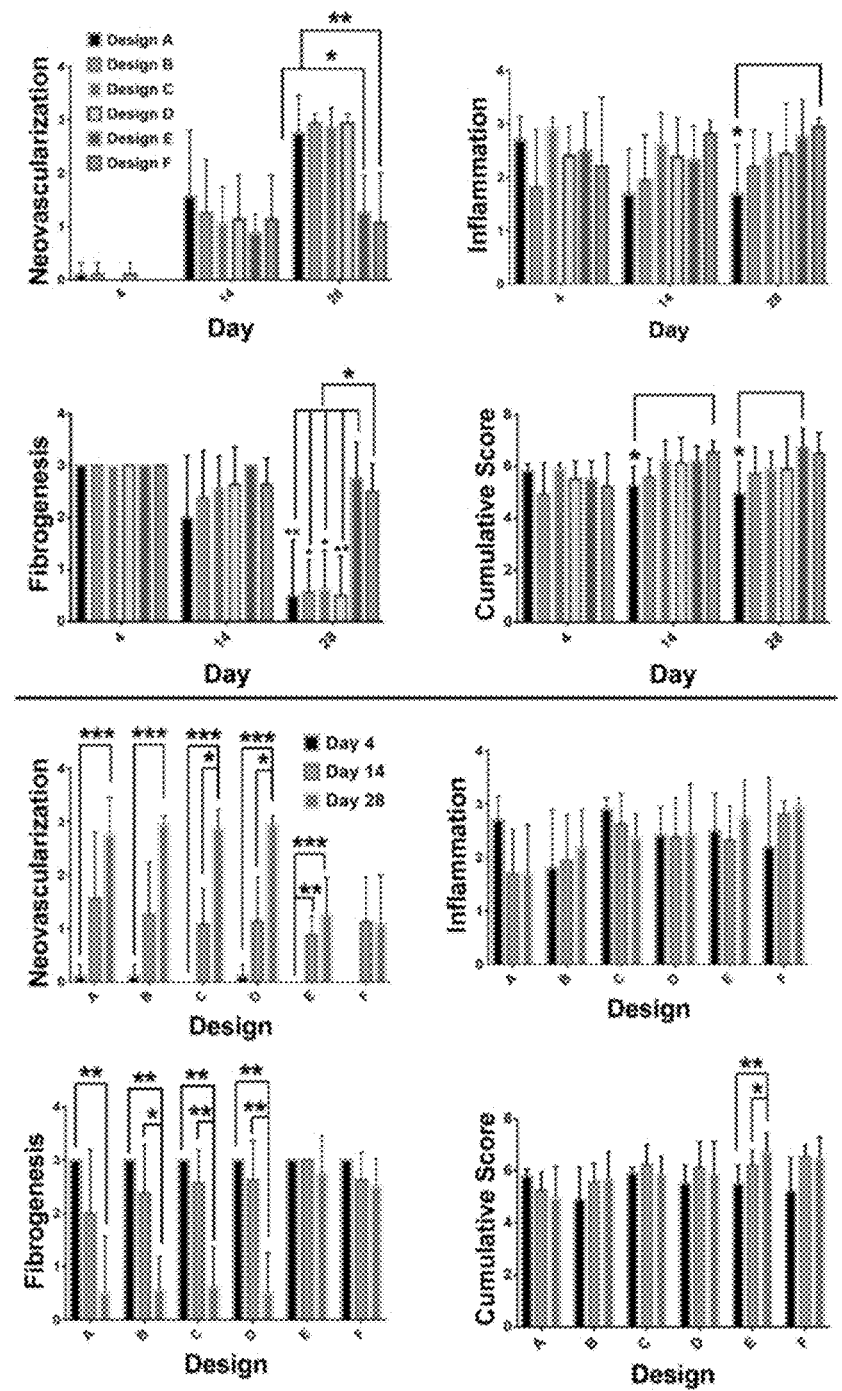
FIG. 11 is a summary of histological scores of a porous scaffold embodiment of the present disclosure.

To determine the respective effect on neovascularization, inflammation, and fibrosis, the porous and nonporous designs were utilized in the same histological scoring schematic of FIG. 4, but this Example utilized time points of Day 4, Day 14, and Day 28. Based on the histological scoring, higher spaced designs (~230 microns) had less intense inflammation than the lower spaced designs (~150 microns). (FIG. 11).

Example 4

To assess and compare neovascularization responses of embodiments of the present disclosure, a microvessel detection algorithm was run that quantified the total number of vessels, total and average vessel area, average vessel perimeter, and microvessel density by colorimetrically detecting DAB that was used to stain against CD31. To quantify neovascularization, deparaffinized slides were first incubated with anti-CD31 (Cat. #DIA-310, Dianova, Hamburg, Germany) for one hour at a 1:100 dilution, then with a biotinylated rabbit anti-rat secondary antibody (Cat. #BA-4000, Vector Laboratories, Inc., Burlingame, Calif.) for 15 minutes at a 1:200 dilution. The Bond Polymer Refine detection system was used for visualization. Slides were dehydrated, cleared and cover slipped before digitally imaging and scanning with an Aperio Versa 200 automated scanning microscope connected to a Leica SCN400 scanner (Leica Microsystems, Wetzlar, Germany). Using the Digital Image Hub, a web-based digital slide-viewing tool provided by the Digital Histology Shared Resource (DHSR) at Vanderbilt University, slides were imaged and quantified for neovascularization via modification of a pre-established, colorimetric-based DAB Microvessel Detection algorithm. The algorithm was optimized and regions of interest (ROIs) were drawn with the aid of a board-certified veterinary pathologist experienced in digital pathology. Algorithm specifications and ROIs were established to maximize specificity for the formation of new blood vessels contained within the tissue reaction site in close proximity (within a few hundred microns) of the polymer surface. Positive background staining of non-vascularized tissue, the polymer surface, and highly-organized, preexisting vessels were excluded from detection as much as possible. Specifications of the algorithm enables exclusion of vessels that are insignificantly small (<60 pixel) or too large in size (>5000 pixel) or aspect ratio (>1000) to be considered representative of a newly formed blood vessel. The algorithm computed total number of vessels, total and average vessel area, average perimeter, and microvessel density.

Figure 12:
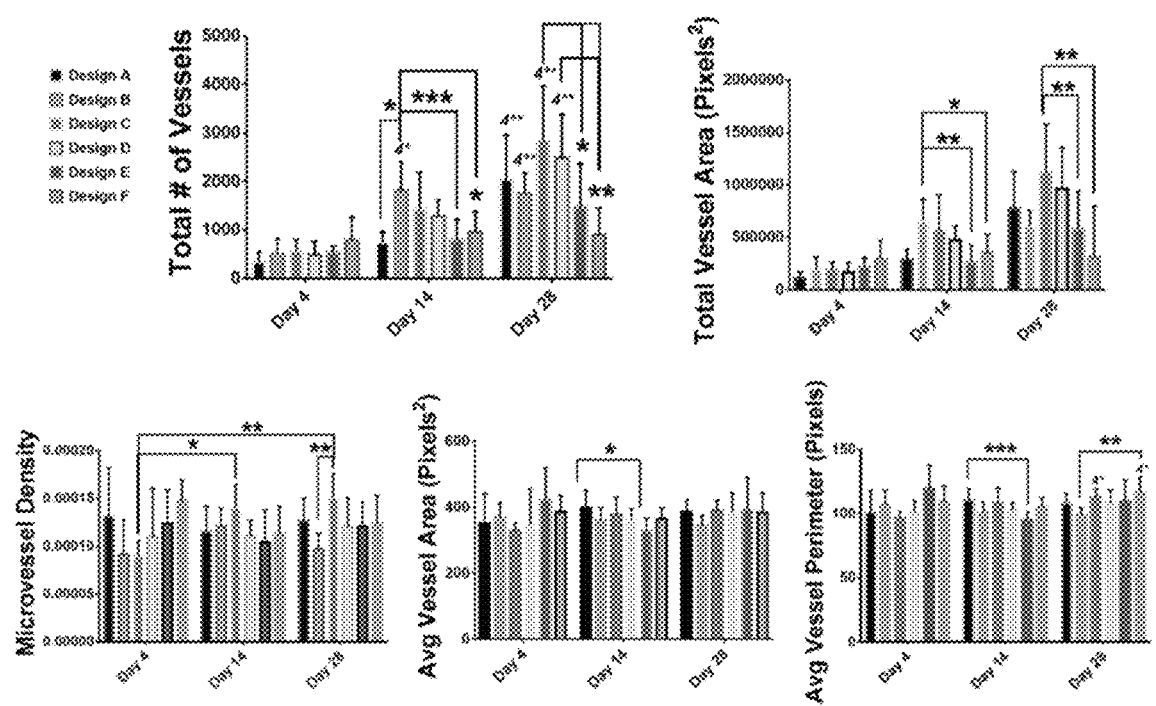
FIG. 12 is a summary of CD31 quantification of neovascularization of a porous scaffold embodiment of the present disclosure.

The same SMP designs were used as in Example 3 along with the same 4, 14, and 28 Day timepoints. It was determined that an external support with approximately 640-micron pores and a pore spacing of approximately 230 microns generated to greatest neovascularization in terms of total number of vessels, vessel area, and vessel density. (FIG. 12).

Example 5

To assess and compare macrophage phenotype characterization of embodiments of the present disclosure, a pan macrophage marker (F4/80), M1 macrophage marker (iNOS), and M2 macrophage marker (CD206) were utilized to characterize macrophage phenotypes of histiocytes observed to be present within tissue constructs to varying degrees, from minimal and part of a foreign body cellular response affecting less than half of the implant circumference, to more marked and part of the formation of a thick cuff around the circumference. Primary antibodies against F4/80 (pan macrophage marker), CD206 (M2 macrophage marker), and iNOS (M1 macrophage marker) were used. Stained slides were digitized using a Pannoramic 250 scanner. A board-certified veterinary pathologist experienced in digital pathology performed tissue image analysis in Aperio ImageScope using the Positive Pixel Count v9 algorithm. All slides were interpreted blinded to experimental conditions. For each antibody, the algorithm was optimized in positive control tissues (primarily mouse spleen, lung, and skin) before applying to the polymer-tissue specimens. For each tissue section, ROIs ranging from 1-12 total per specimen were defined prior to analysis. Depending on chronicity of the tissue response, the 50-150 μm surrounding an implant was selected for analysis, specifically excluding any undesired positively labeled structures or artifacts such as hair shafts or nonspecific DAB staining of the polymer material. Parameters reported for each specimen represent measures of positivity, which approximates the expression of a given protein within a tissue section. The output of positivity was defined for a given ROI as:

$$\% \text{ Positivity} = \frac{\text{Total \# of moderately or strongly positive pixels}}{\text{Total \# of pixels}} \times 100\%$$

Depending on the signal to noise ratio of the stain, weakly positive pixels were also included as positive in some of the samples. Macrophage phenotype was further characterized by the ratio of M2 (CD206+) to M1 (iNOS+) cells:

$$M2:M1 = \frac{\text{\# of } M2 \text{ cells}}{\text{\# of } M1 \text{ cells}}$$

Macrophages are phagocytic cells that are central to the inflammatory response as they are recruited to damaged or disrupted tissue sites through chemotaxis. They secrete a vast array of stimulating factors themselves to regulate the inflammatory response in a number of ways. Depending on their function as a pro-inflammatory or wound healing stimulator, they tend to be classified into two broad categories, pro-inflammatory M1 and pro-wound healing M2, but also have several subset phenotypes and are quite fluid in nature. In general, it is understood that a shift from a "classically-activated," pro-inflammatory M1 macrophage phenotype to an "alternatively-activated," pro-tissue remodeling M2 macrophage phenotype indicative of constructive wound healing responses such as neovascularization. Although macrophage phenotype characterization of external supports is currently underexplored and largely unknown, it is hypothesized that this shift from M1 to M2 over 28 days is desirable to fully resolve tissue and promote neovascular effects that are favorable towards reducing neointimal hyperplasia. For example, a recent study evaluating murine laser-induced choroidal neovascularization demonstrated that new blood vessel formation correlated with a transient upregulation in M1 phenotype followed by a sustained shift to M2. However, macrophage phenotypes exist across a diverse spectrum and some recent studies have found that both M1 and M2 phenotypes are significantly upregulated in scaffolds such as glutaraldehyde-crosslinked ones that exhibited an increase in new blood vessel formation after 10 days when implanted in subcutaneous mouse tissue. Inflammation has been shown to be beneficial for neovascularization, such as when bone marrow mononuclear cells (BMCs) promoted early monocyte recruitment by secreting significant amounts of monocyte chemoattractant protein-1, which help tissue engineered vascular grafts (TEVGs) transform into functional neovessels. In most contexts, ePTFE is a relatively inert polymer owing to its strong carbon-fluoride bond and non-degradability. In its microporous format, it exhibited minimal adhesion with a mean implantation lifetime of 420 days after laparoscopic ventral hernia repair in 65 repoerative patients, and it also reduced adhesions in a rabbit peritoneal model of laparoscopic ventral hernia repair relative to polypropylene and HA/polypropylene meshes. It did not promote the substantial inflammatory and neovascularization response that Dacron external meshes did when applied to porcine vein grafts and was ineffective in this context while Dacron meshes correspondingly reduced neointimal formation. Meanwhile, the specific roles that macrophages play in fibrogenesis are largely unknown, but fibrotic lesions are accompanied by a high degree of chronic inflammatory cell infiltration where monocytes and macrophages are present. ePTFE also exhibited less neovascularization and fibrogenesis than the PCL-ACPCL scaffolds in this study, so it was anticipated that it would have less macrophages.

Figure 13:
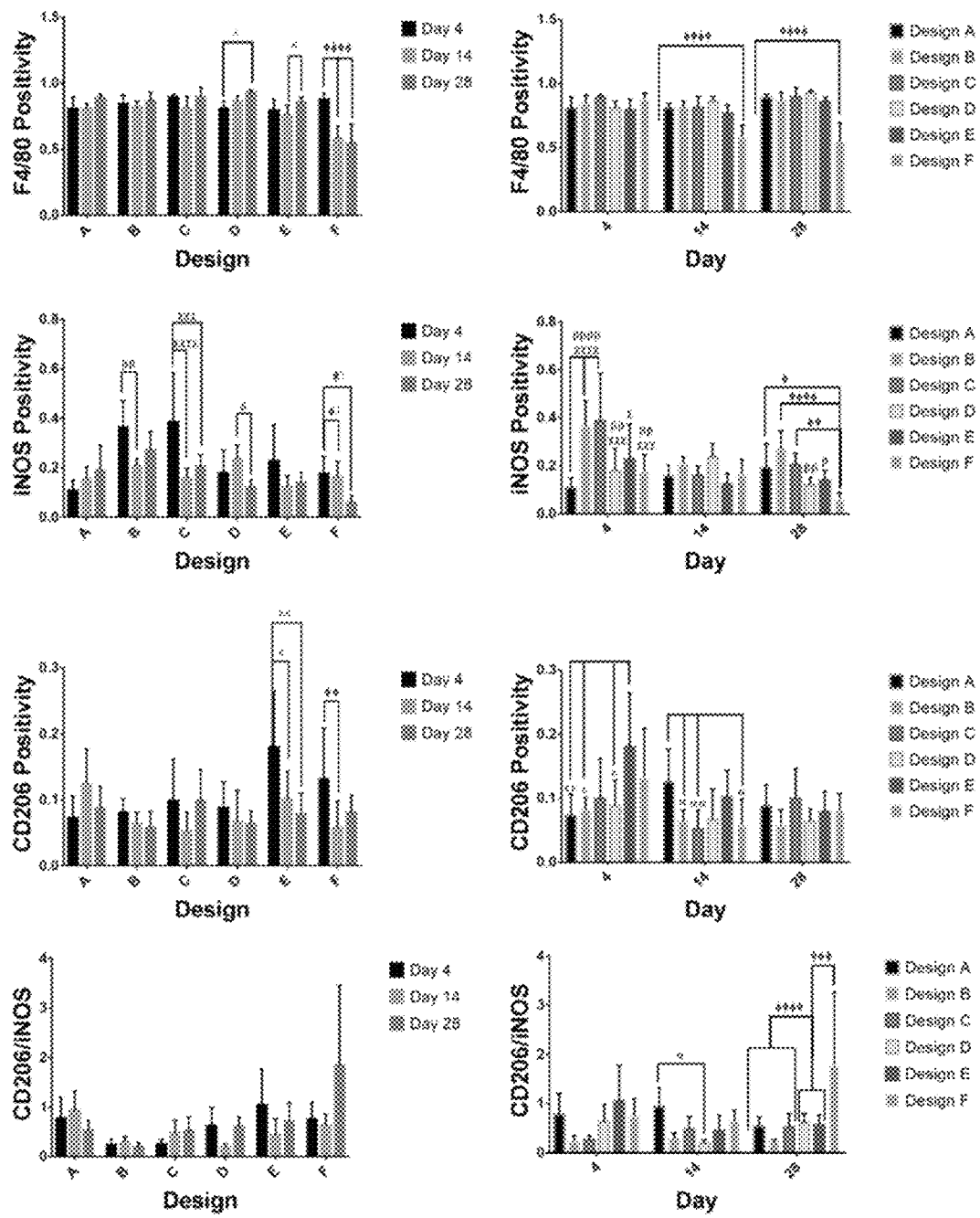
FIG. 13 is a summary of Macrophage Phenotype characterization of a porous scaffold embodiment of the present disclosure.

As shown in FIG. 13, the iNOS positivity was significantly lower for Design A relative to Designs B and C, which implies that larger pore sizes and spacings may promote an M1 macrophage phenotype at early timepoints; this transient upregulation of an M1 phenotype at early stages has been shown to promote neovascularization. Conversely, scaffolds which promote an eventual switch toward an M2 macrophage phenotype are expected to fully resolve their wound healing process. On Day 28, Design D had significantly lower iNOS positivity than Design B, which implies that the wider-spaced design (D) may better promote wound healing resolution. Combining staining data of groups based on equivalent pore size and spacing revealed some interesting insights with regards to this characterization of macrophage phenotype. On Day 14, smaller pores (A+C, 635 μm diameter) exhibited significantly greater CD206 positivity (mean difference=0.0452, p=0.141), lower iNOS positivity (mean difference=−0.0655, p=0.0017), and a higher CD206/iNOS ratio (mean difference=0.463, p=0.0004) than larger pores (B+D, 1160 μm diameter). On Day 28, smaller pores again were more positive for CD206 (mean difference=0.0322, p=0.0147), while larger spacings (C+D, 230 μm) had significantly lower iNOS positivity (mean difference=0.0687, p=0.0304). No differences were detected for F4/80 positivity. Taken together, this implies that the ~635 μm diameter, ~230 μm spacing group (Design C) elicits an inflammatory response characterized by more of the "tissue remodeling" M2 phenotype. This also coincides with the design exhibiting the greatest amount of neovascularization as measured by total blood vessel number, total vessel area, and microvessel density by the CD31 microvessel detection algorithm.

Example 6

To assess the wound healing process of embodiments of the present disclosure, matrix metalloproteinases (MMPs) were analyzed through staining to detect localization to the polymer-tissue interface. Tissue sections containing the polymer-tissue interface were immunohistochemically stained for MMPs 3, 9, 12, 13, and 14, as all of these MMPs were detected from proteomics analysis of tissue extracts and are known to play a role in the wound healing process. Cells labeled positively for MMPs are separated into those observed immediately adjacent to the implant (within approximately 100 μm distance) and the associated reactive neotissue ("peri-polymer localization"), and those observed at a greater distance, separated by a fascial plane ("other cells labeled"). (FIG. 14). For each, cell types are listed from strongest/most intense staining to weakest/least intense staining. Granular, cytoplasmic staining for MMPs was observed in several cell types in the experimental tissue specimens, but notably co-localized with macrophages peripheral to the polymer-tissue implant the strongest of any other cell type. This implies that MMPs are secreted by macrophages that infiltrate the polymer-tissue interface. MMP-9 primarily digests gelatin and has been shown to be secreted in high levels by M2 macrophages known to promote angiogenesis, especially by the M2c subgroup. MMP-3 and MMP-9, along with MMP-1, are known to regulate the most widespread array of chemokine signals that are important drivers of the inflammatory response. IHC staining of MMP-9 co-localized with monocyte/macrophages and multinucleated giant cells, as did all of the MMPs. (FIG. 15).

Example 7

To assess the cellular and protein response of embodiments described herein, a proteomics analysis was done to determine protein regulation and responses. Sections of the tissue-scaffold explants were immediately placed in a cryovial and submerged for approximately 1 minute to flash freeze the tissue. Samples were then kept on dry ice for a short period of time before transferring to a −80° C. freezer. Tissue samples were then thawed, immediately cut finely with a sterile surgical blade, and submerged in an NP-40 lysis buffer cocktail (10 mL of 50 mM Tris, 150 mM NaCl, pH 7.8 with 1% NP-40 added to protease inhibitor cocktail P2714-10TL from Sigma) under sonication for 2-3 minutes. The turbid solution was spun down at 2000 g for 2 minutes and the supernatant was transferred to a separate vial for storage at −80° C. Protein concentrations of the lysed tissue samples were determined by BCA assay.

Protein homogenates (50 ug) were precipitated with ice-cold acetone overnight at −20° C. The samples were centrifuged at 14,000 g at 4° C. for 30 minutes, and the precipitated protein pellets were washed with cold acetone, dried, and reconstituted in 500 mM Tris with 50% Trifluoroethanol (TFE). Protein lysates were reduced with TCEP and available cysteine residues were alkylated with Iodoacetamide. Next, lysates were diluted 10-fold with Tris to obtain a final concentration of 10% TFE, and proteins were digested with sequencing-grade trypsin at 37° C. overnight.

Following digestion, protein digests were diluted 9-fold with 0.1% formic acid and each sample was analyzed by LC-coupled tandem mass spectrometry (LC-MS/MS). An analytical column (360 µm O.D.×100 µm I.D.) was packed with 24 cm of C18 reverse phase material (Jupiter, 3 µm beads, Phenomenex) directly into a laser-pulled emitter tip. Peptides aliquots (1.2 ug of digested protein) were loaded on the capillary reverse phase analytical using a Dionex Ultimate 3000 nanoLC and autosampler and were introduced via nano-electrospray into a Q Exactive Plus mass spectrometer (Thermo Scientific, San Jose, Calif.). Each sample was analyzed using a 2-hour LC gradient. The Q Exactive Plus was operated in data-dependent mode, and the instrument method consisted of an MS1 scan following by up to 20 HCD MS/MS scans. Normalized collision energy was set to 27, dynamic exclusion was set to 30 s, and peptide match and isotope exclusion were enabled.

Comparisons of relative peptide and protein amounts were performed using MaxQuant-LFQ software. It utilizes full-scan peptide intensity determination and normalization both within and across samples. Missing values were imputed and cross group significance estimated via t-test with benjamini-hochberg correction for multiple testing. For simplicity of comparison, macroporous designs A-D were grouped together and compared against non/microporous group designs E-F. (FIG. 16).

It will be understood that various details of the presently disclosed subject matter can be changed without departing from the scope of the subject matter disclosed herein. Furthermore, the description provided herein is for the purpose of illustration only, and not for the purpose of limitation.

While the terms used herein are believed to be well understood by one of ordinary skill in the art, the definitions set forth herein are provided to facilitate explanation of the presently disclosed subject matter.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

The terms "comprising", "including," and "having" are intended to be inclusive and mean that there may be additional elements other than the listed elements.

Following long-standing patent law convention, the terms "a", "an", and "the" refer to "one or more" when used in this application, including the claims. Thus, for example, reference to "a polymer" includes a plurality of such polymers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, references are mentioned. All such references are incorporated herein by reference.

Thus, although there have been described particular embodiments of the present invention of a new and useful POLYMERIC VASCULAR GRAFTS WHICH INDUCE NEOVASCULARIZATION WITH MILD TO MINIMAL INFLAMMATION AND PROMOTION OF FIBROVASCULAR TISSUE it is not intended that such references be construed as limitations upon the scope of this invention except as set forth in the following claims.

What is claimed is:

1. An implantable tissue supporting device comprising:
  a biodegradable polymeric scaffold capable of surrounding a tissue, the biodegradable polymeric scaffold includes at least one polymer, the at least one polymer comprising at least one monomer that is crosslinkable, wherein the biodegradable polymeric scaffold is configured to have a melting temperature and be moldable from a first shape to a second shape by an external force when the melting temperature is met or exceeded, wherein the device is mechanically compliant at from about 20 to about 50° C., and wherein the biodegradable polymeric scaffold has a pore size of about 500-750 µm and a pore spacing of about 220 µm to about 250 µm.

2. The device of claim 1, wherein the scaffold has a pore size of about 600-700 µm, and a pore spacing of about 230 µm.

3. The device of claim 1, wherein the at least one monomer is allyl functionalized and includes an allyl carboxylate group.

4. The device of claim 1, wherein the at least one monomer includes ε-caprolactone.

5. The device claim 1, wherein the biodegradable polymeric scaffold comprises a plurality of crosslinked polymers, the plurality of crosslinked polymers includes a poly(ε-caprolactone)-co-(α-allyl carboxylate ε-caprolactone) polymer.

6. The device of claim 5, wherein the plurality of crosslinked polymers include about 1 mol % to about 30 mol % of poly(ε-caprolactone).

7. The device of claim 1, wherein the device has 50-100% shape fixity, and 50-100% shape recovery.

8. The device of claim 1, wherein the device is configured to include a Young's modulus at 37° C. of about 0.05-200 MPa.

9. The device of claim 1, wherein the tissue is a vein or artery.

10. The device of claim 9, wherein the device is external to the vein or artery.

11. The device of claim 1, wherein the device is configured such that it retains a shape to fit around said tissue when implanted.

12. The device of claim 1, wherein the device is external to a vascular graft anastomosis.

13. The device of claim 1, wherein the device forms a seamless and sutureless sheath.

14. The device of claim 1, wherein the device has resilient radial expression in a manner that mimics the compliance properties of said tissue.

15. The device of claim 14, wherein the device is deformable by at least one of stretching or bending along its length to conform to the shape of the tissue.

16. The device of claim 1, wherein the biodegradable polymeric scaffold further comprises a shape memory polymer.

17. The device of claim 16, wherein the shape memory polymer has a melting temperature at or near body temperature.

18. The device of claim 1, wherein the biodegradable polymeric scaffold includes the at least one monomer that is photocrosslinkable and further includes at least a second monomer that is not photocrosslinkable.

19. The device of claim 1, wherein the biodegradable polymeric scaffold includes the at least one monomer being allyl-functionalized and further includes at least one second monomer that is not allyl-functionalized.

20. The device of claim 1, wherein the biodegradable polymeric scaffold is maintained at least 3 months after implantation.

* * * * *

UNITED STATES PATENT AND TRADEMARK OFFICE
CERTIFICATE OF CORRECTION

| | |
|---|---|
| PATENT NO. | : 11,305,039 B2 |
| APPLICATION NO. | : 16/824674 |
| DATED | : April 19, 2022 |
| INVENTOR(S) | : Timothy C. Boire |

It is certified that error appears in the above-identified patent and that said Letters Patent is hereby corrected as shown below:

In the Specification

Replace third paragraph on Column 1, with the following:
Government Support
This invention was made with government support under grant number HL122347 awarded by the National Institutes of Health. The government has certain rights in the invention.

Signed and Sealed this
Fifth Day of September, 2023

Katherine Kelly Vidal
*Director of the United States Patent and Trademark Office*